United States Patent [19]

Willis

[11] Patent Number: 4,711,235

[45] Date of Patent: Dec. 8, 1987

[54] INTRAVAGINAL DEVICE

[76] Inventor: Robert E. Willis, 6606 N. Saginaw, Flint, Mich. 48505

[21] Appl. No.: 896,316

[22] Filed: Aug. 13, 1986

Related U.S. Application Data

[63] Continuation of Ser. No. 658,279, Oct. 5, 1984, abandoned, which is a continuation-in-part of Ser. No. 452,449, Dec. 23, 1982, abandoned, which is a continuation of Ser. No. 215,624, Dec. 12, 1980, abandoned.

[51] Int. Cl.4 ............................................. A61F 5/46
[52] U.S. Cl. .................................................. 128/130
[58] Field of Search ................................. 128/127–131

[56] References Cited

U.S. PATENT DOCUMENTS

| | | | |
|---|---|---|---|
| 2,310,564 | 2/1943 | Younkins | 128/127 |
| 3,169,894 | 2/1965 | Monett | 128/127 |
| 4,198,965 | 4/1980 | Strickman et al. | 128/127 |
| 4,326,510 | 4/1982 | Buckles | 604/55 |

Primary Examiner—C. Fred Rosenbaum
Assistant Examiner—Denise Whelton
Attorney, Agent, or Firm—Marshall & Melhorn

[57] ABSTRACT

An intravaginal contraceptive device formed of a ring having a central sheet of resilient impermeable material sandwiched between two layers of foam rubber. The foam rubber traps sperm and bacteria in a vaginal recess for a time sufficient to be destoyed by the normal acid pH of the vaginal secretions. The ring defines the sheet material into a cup-shape with four sides, one pair of opposing sides including a wire core inwardly bent and another pair of sides with one outwardly rounded and the other having a fork configuration. A normally closed flap valve is formed in the sheet with an attached extension for opening the flap.

8 Claims, 6 Drawing Figures

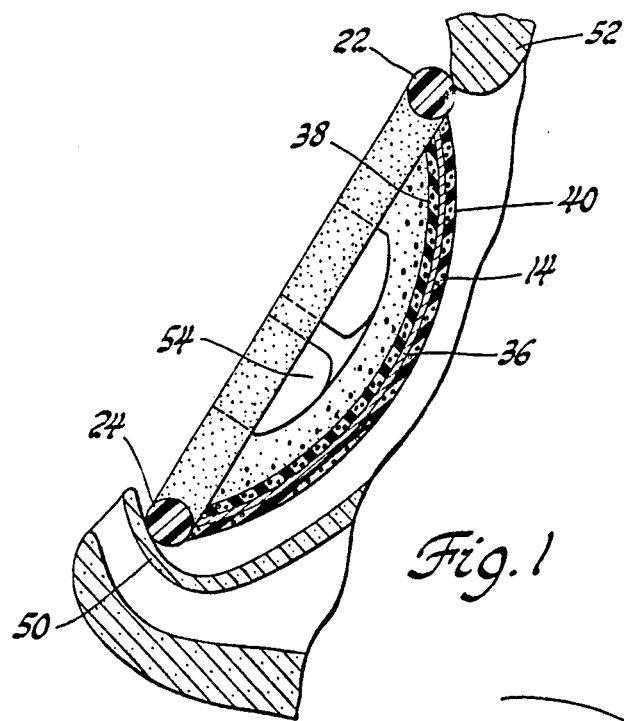
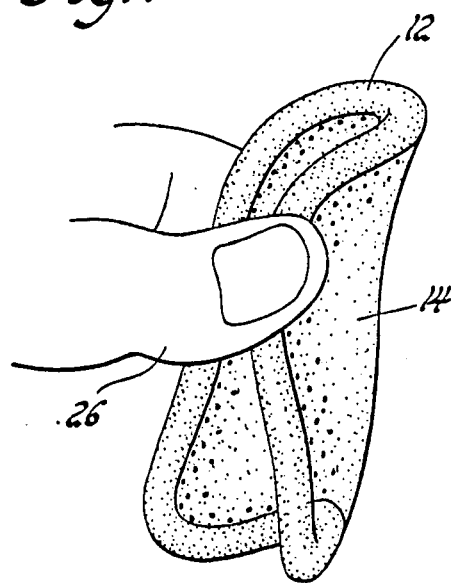
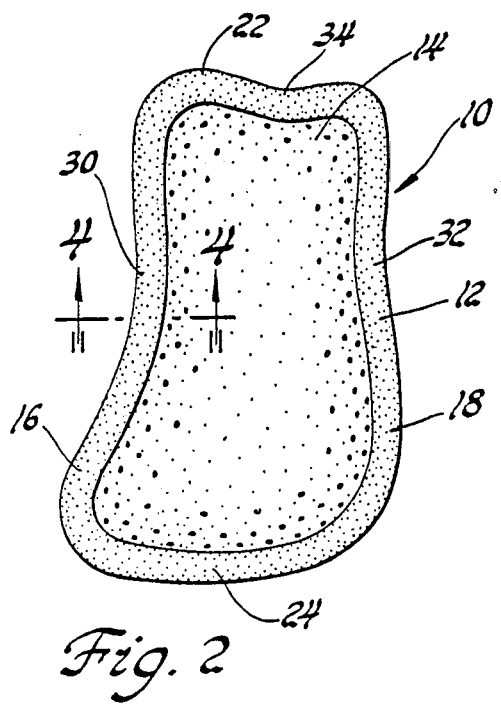
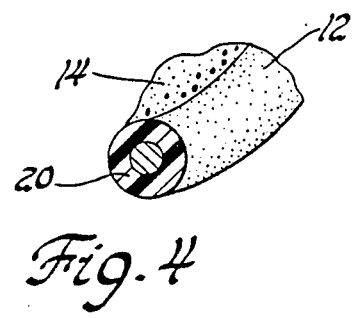

INTRAVAGINAL DEVICE

CROSS-REFERENCE TO RELATED APPLICATIONS

This application is a continuation of U.S. patent application Ser. No. 658,279, filed 10/5/84, now abandoned which is a continuation-in-part of copending U.S. patent application Ser. No. 452,449, filed Dec. 23, 1982, now abandoned, which is a continuation of U.S. patent application Ser. No. 215,624, filed Dec. 12, 1980, now abandoned.

BACKGROUND OF THE INVENTION

The present invention relates to a reuseable intravaginal barrier.

There are many forms of intravaginal devices which have specialized uses. One such device is the reuseable cervical pessary which is utilized to prevent contraception. Typical pessaries include the diaphragm, the cervical cap, the vault cap and the vimule. Another type of intravaginal device is the tampon which is utilized to absorb the flow of menses.

U.S. Pat. No. 2,522,822 issued to H. E. Harris discloses a disposable uterine pessary. The device is formed of a pad of partially compressed, fibrous material with a highly compressed peripheral bead surrounding the pad and maintaining the shape thereof. A cuplike cavity formed in the forward portion of the pad, two diagonally extending, indented grooves formed in the pad and extending outwardly and rearwardly from the cavity, and a substantially triangular, resilient apron portion closing the rear portion of the cavity between the indented grooves cooperate so that when the sides of the pessary are compressed toward each other, the apron portion will bow rearwardly to form a receiving socket for receiving the vaginal neck of the uterus.

U.S. Pat. No. 3,169,894 discloses a diaphragm comprising a dome or a receptacle body portion having a rim enclosing a continuous coil spring. Two curved or arched pin sections are arranged in the coils of the spring in an opposed relationship to each other. The pins are shaped to conform to the diameter contour of the spring and to maintain this contour in the rigid state even when the diaphragm is flexed.

U.S. Pat. No. 3,261,353 issued to T. H. Johnson discloses vaginal devices which are formed from a laminated sheet of natural or synthetic rubber foam or other plastic foam which is laminated or cemented to a lightly cured surgical gum rubber diaphragm. The rubber or other organic foam laminate then is saturated by alternate compression and release of spermicidal chemicals which may also contain anti-venereal agents and lubricants.

U.S. Pat. No. 3,371,664 issued to N. Pleshette discloses an intravaginal diaphragm having a circular peripheral frame formed of a flexible material. Attached to the frame is a relatively thin membrane of elastomeric material and a removal band connected to extend across the perimeter of the frame and adjacent thereto so as to produce an optimum change in the operative shape to facilitate removal of the diaphragm.

U.S. Pat. No. 4,198,965 issued to R. L. Strickman et al. discloses a disposable contraceptive cervical barrier formed in one or more layers in the form of standard pessaries with at least one layer impervious to the passage of sperm, with a medicament such as a spermicide, germicide, or an abortion inducing agent either impregnated into a foam plastic layer or in the form of a layer of gel or powder, the medicament being activatible upon contact with an aqueous solution.

U.S. Pat. No. 4,428,370 issued to P. G. Keely discloses an insertion unit for a vaginal diaphragm. The diaphragm has a stiff resilient rim and the interior surface of the diaphragm could be provided with a spermicidal substance.

SUMMARY OF THE INVENTION

The present invention concerns an intravaginal device which functions as a reuseable barrier. A central sheet of resilient impermeable material has a supporting ring attached to a border of the sheet to force the sheet into a cup-shape with four sides. One pair of opposing sides has a wire core in the ring portion and the sides are inwardly bent in a central portion thereof. The other pair of opposed sides has one side outwardly rounded and the other side in a fork or inwardly rounded configuration. A user can squeeze the sides with the wire core to move such sides adjacent one another to aid in the insertion and removal of the device.

The central sheet can be formed of a rubber material with a layer of foam rubber attached to both surfaces to trap sperm and bacteria. An opening can be formed in a central portion of the sheet material and covered by a flap to form a normally closed flap valve. An extension formed on the flap can be utilized to open the valve to release trapped material or insert medicaments without removing the device.

It is an object of the present invention to provide an intravaginal barrier device which can be reused.

It is another object of the present invention to provide an intravaginal device which does not have to be removed to permit release of a bodily discharge or the insertion of a medicament.

These and still further objects and advantages of the invention will become readily apparent to those skilled in the art to which the invention pertains upon reference to the following detailed description.

DESCRIPTION OF THE DRAWINGS

The description refers to the accompanying drawings in which like reference characters refer to like parts throughout the several views, and in which:

FIG. 1 illustrates a cross section of a preferred intravaginal device, in use;

FIG. 2 is a perspective view of the preferred device;

FIG. 3 is a view illustrating how the device may be squeezed to a fraction of its normal width;

FIG. 4 is a cross-sectional view taken along line 4—4 of FIG. 3;

DESCRIPTION OF THE PREFERRED EMBODIMENT

Figure 5:
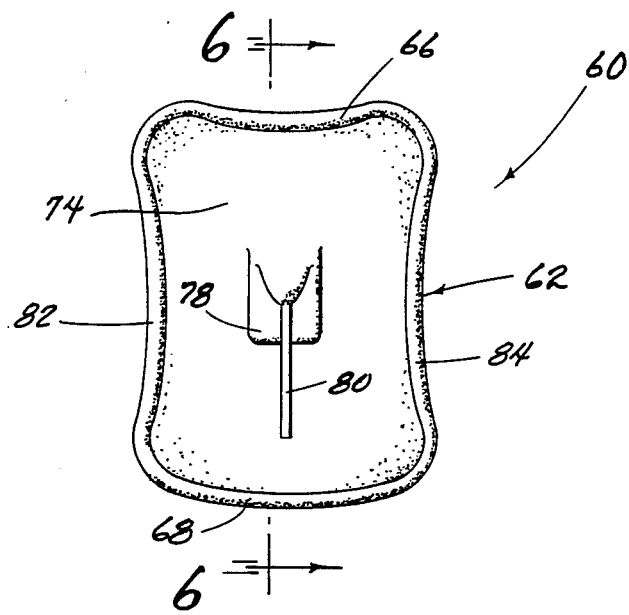
FIG. 5 is a front elevational view of an alternate embodiment of the present invention.

Referring to the drawing, FIG. 2 illustrates a preferred intravaginal device 10 comprising a ring 12 attached to the border of a cup-shaped sheet 14.

Ring 12 is preferably formed of a resilient material, such as a neoprene non-absorbent rubber material, and has a generally four-sided shape with sides 16 and 18 having a wire core 20 as illustrated in FIG. 4. The other two sides 22 and 24 have a central section without wire core as illustrated in FIG. 1. The user, by squeezing the ring with fingers 26, as illustrated in FIG. 3, can move sides 16 and 18 closely adjacent one another. The stiff wire core in sides 16 and 18 prevent sides 22 and 24 from being moved toward one another.

Sides 16 and 18 are bent inwardly as at 30 and 32, and side 24 has a generally rounded configuration while side 22 has a slight fork or inwardly rounded configuration as illustrated at 34. The diameter of the ring element is about three-eighths of an inch. The overall size of the ring is chosen to accommodate the size of the user.

Sheet 14 is preferably formed of a rubber material and includes a central impermeable membrane 36.

A layer 38 of foam rubber is attached to one side of membrane 36 and a second layer 40 of foam rubber is attached to the other side of the membrane. Both layers 38 and 40 are each approximately one-eighth of an inch thick and formed of a foam rubber adapted to trap sperm and bacteria.

FIG. 1 illustrates the manner in which the device is mounted with one side adjacent the rear wall 50 of the vaginal recess and the opposite side adjacent the pubic bone 52 such that sheet 14 provides a barrier to cervix 54. The user can squeeze the ring in the manner illustrated in FIG. 3 for insertion or removal of the device. The shape of the ring is such that it can be easily inserted into the vagina to remain there for a month. The ring, although preferably formed of a neoprene rubber, can also be formed of a plastic material. The device can be periodically removed, washed, and reinserted for reuse. The manufacturing cost is inexpensive so that it can be discarded if necessary.

Although a spermicidal gel or spray can be used, it is believed that the natural ability of the vaginal secretions to form an acid pH which will kill both sperm and bacteria makes such spermicide material unnecessary.

Figure 6:
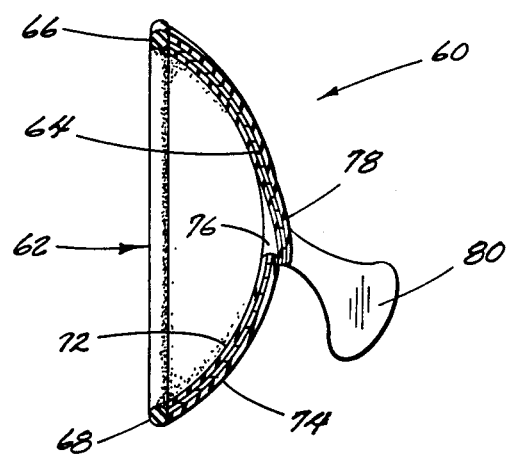
FIG. 6 is a cross-sectional view taken along the line 6—6 of FIG. 5.

There is shown in FIGS. 5 and 6 an alternate embodiment of the present invention. An intravaginal device 60 comprises a ring 62 attached to the border of a cup-shaped sheet 64. A layer 72 of foam rubber can be attached to one surface of the sheet 64 and another layer 74 of foam rubber can be attached to the other surface of the sheet. The device 60 is generally four-sided with an upper side 66 having a generally fork or inwardly rounded shape, a lower side 68 having a generally outwardly rounded shape, and a pair of opposed sides 82 and 84 each being inwardly bent in a central portion thereof.

The sheet 64 has a central opening 76 formed therein for the release of bodily fluids or the insertion of medicaments. The opening 76 is normally closed by a flap 78 forming a valve. An extension 80 formed on the flap 78 can be utilized to selectively actuate or operate the valve by pulling the flap 78 away from the opening 76. Once the valve is open, bodily fluids can be discharged without removing the device 60. Also, medicaments can be inserted through the opening 76 and retained by the device 60.

In accordance with the provisions of the patent statutes, the principle and mode of operation of the invention have been described and illustrated in its preferred embodiments. However, it must be understood that the invention can be practiced otherwise than as specifically illustrated and described without departing from its spirit or scope.

What is claimed is:

1. An intravaginal device comprising:
   a sheet member of flexible, fluid-impermeable material;
   a normally closed flap valve formed in said sheet member, said flap valve having an extension for actuating said flap valve between said normally closed position and an open position; and
   a supporting ring formed of a first resilient material attached to a border of said sheet material to force said sheet material into a cup-shape with four sides, one pair of opposing ones of said sides including a core formed of a second resilient material defining said ring sides as inwardly bent in a central area thereof, and another pair of said sides opposite one another formed entirely of said first resilient material, one said side being outwardly rounded and the other said side having an inwardly rounded configuration.

2. The device according to claim 1 including a foam rubber layer attached to each of two opposing surfaces of said sheet member.

3. The device according to claim 2 wherein said sheet member is formed of a rubber material.

4. The device according to claim 1 wherein said one pair of opposed sides can be moved to a position adjacent one another.

5. An intravaginal device comprising:
   a sheet member of flexible, fluid-impermeable material including porous material attached to opposite sides of said sheet member;
   a supporting ring attached to a border of said sheet member;
   a normally closed flap valve formed in said sheet member; and
   an extension attached to said flap valve and extending outwardly from a surface thereof for actuating said flap valve between said normally closed position and an open position, and wherein said supporting ring is formed of a first resilient material and forces said sheet member into a generally cup-shaped rectangle having a first pair of opposed sides with a core formed of a second resilient material inwardly bent in a central area thereof and a second pair of opposed sides formed entirely of said first resilient material, one being outwardly rounded and another having an inwardly rounded configuration.

6. The device according to claim 1 wherein said first resilient material is neoprene material and said second resilient material is a stiff wire material.

7. An intravaginal device comprising:
   a sheet member of flexible, fluid-impermeable material;
   a normally closed flap valve formed in said sheet member including an extension attached to said flap valve for actuating said flap valve between a normally closed position and an open position; and
   a supporting ring formed of a first resilient material attached to a border of said sheet material to force said sheet material into a cup-shaped with four sides, one pair of opposing ones of said sides including a core formed of a second resilient material defining said one pair of opposing sides as inwardly bent in a central area thereof, and another pair of said sides opposite one another formed entirely of said first resilient material, one side of said another pair being outwardly rounded and the other side of said another pair having an inwardly rounded configuration.

8. The device according to claim 7 wherein said first resilient material is neoprene material and said second resilient material is a stiff wire material.

* * * * *